United States Patent
Zhang et al.

(10) Patent No.: US 9,545,236 B2
(45) Date of Patent: Jan. 17, 2017

(54) METHOD FOR SCANOGRAM SCANS IN PHOTON-COUNTING COMPUTED TOMOGRAPHY

(71) Applicant: TOSHIBA MEDICAL SYSTEMS CORPORATION, Otawara-shi (JP)

(72) Inventors: Yuexing Zhang, Naperville, IL (US); Satoru Nakanishi, Arlington Heights, IL (US); Xiaolan Wang, Buffalo Grove, IL (US)

(73) Assignee: Toshiba Medical Systems Corporation, Otawara-shi (JP)

(*) Notice: Subject to any disclaimer, the term of this patent is extended or adjusted under 35 U.S.C. 154(b) by 102 days.

(21) Appl. No.: 14/604,408

(22) Filed: Jan. 23, 2015

(65) Prior Publication Data
US 2016/0213340 A1   Jul. 28, 2016

(51) Int. Cl.
A61B 6/03    (2006.01)
A61B 6/00    (2006.01)
G01N 23/00   (2006.01)
G01N 23/04   (2006.01)
H05G 1/00    (2006.01)
G06T 11/00   (2006.01)

(52) U.S. Cl.
CPC .............. *A61B 6/482* (2013.01); *A61B 6/032* (2013.01); *A61B 6/488* (2013.01)

(58) Field of Classification Search
USPC .......... 378/4, 9, 11, 13, 14, 19; 250/370.08, 250/370.09, 370.1
See application file for complete search history.

(56) References Cited

U.S. PATENT DOCUMENTS

| | | | | |
|---|---|---|---|---|
| 7,822,169 | B2* | 10/2010 | Roessl | G06T 5/50 378/4 |
| 8,031,828 | B1* | 10/2011 | DeMan | G06T 11/005 378/15 |
| 8,862,206 | B2* | 10/2014 | Wang | 378/21 |
| 2004/0264626 | A1* | 12/2004 | Besson | A61B 6/508 378/4 |
| 2010/0204942 | A1* | 8/2010 | Danielsson | G01T 1/243 702/85 |
| 2011/0211667 | A1* | 9/2011 | Ikhlef | A61B 6/032 378/19 |
| 2011/0282181 | A1* | 11/2011 | Wang | A61B 5/0095 600/407 |
| 2014/0226783 | A1* | 8/2014 | Ning | A61B 6/4241 378/5 |
| 2015/0346354 | A1* | 12/2015 | Arakita | G01T 1/1606 378/19 |
| 2016/0022235 | A1* | 1/2016 | Ning | A61B 6/032 378/4 |

* cited by examiner

*Primary Examiner* — Bernard Souw
(74) *Attorney, Agent, or Firm* — Oblon, McClelland, Maier & Neustadt, L.L.P.

(57) ABSTRACT

A computed tomography (CT) imaging apparatus includes an X-ray source to emit X-rays; a plurality of photon-counting detectors (PCDs) arranged in a circular ring between the X-ray source and a CT detector; and processing circuitry to cause the X-ray source and the CT detector to perform a helical scan of an object to obtain projection data; extract, from the obtained projection data, a plurality of sets of projection data corresponding to a plurality of X-ray tube positions of the helical scan; and combine the plurality of sets of extracted projection data to obtain a scanogram.

14 Claims, 10 Drawing Sheets

X-ray passes through between two nearest PCDs

METHOD FOR SCANOGRAM SCANS IN PHOTON-COUNTING COMPUTED TOMOGRAPHY

FIELD

The exemplary embodiments described herein relate to computed tomography (CT) systems with photon-counting detectors (PCDs).

BACKGROUND

Traditional CT scanners use energy-integrating detectors for acquiring energy integration X-ray data. An energy-integrating detector does not take advantage of the energy information in the X-ray beam. Even though the X-ray source emits X-rays in a broad spectrum, the detector is not able to differentiate between photons of different energy, but delivers an output signal proportional to the total energy of the photons registered during the readout interval. To obtain the spectral nature of the transmitted X-ray data, a photon-counting detector splits the X-ray beam into its component energies or spectrum bins and counts a number of photons in each of the bins. The use of the spectral nature of the X-ray source in CT is often referred to as spectral CT. Spectral CT imaging provides material separation capabilities that can potentially enable new clinical applications. The spectral images are usually presented as material concentration images of basis materials or monoenergetic images. For example, spectral CT is used in discriminating tissues, differentiating between materials such as tissues containing calcium and iodine, or enhancing the detection of smaller vessels. Among other advantages, spectral CT is also expected to reduce beam-hardening artifacts and to increase accuracy in CT numbers independent of scanners.

Currently, most conventional designs acquire spectral information using either high- and low-energy X-ray sources. To improve the accuracy of material separation, photon-counting detector technologies can be used to provide good energy resolution. Photon-counting energy-resolved direct-conversion semiconductor detectors for computed tomography (CT) allow exploitation of the spectral information of each incident photon. X-ray photons interacting with the semiconductor sensors can be converted directly to electron-hole pairs without any inefficient intermediate processes, ensuring the superior intrinsic energy resolution. However, for conventional photon-counting CT, sparsely distributed stationary photon-counting detectors are distributed in front of a third-generation integrated detector, and create shadows on the third-generation integrated detector during scanogram scans. These shadows severely degrade the quality of the scanogram images.

BRIEF DESCRIPTION OF THE DRAWINGS

A more complete appreciation of the teachings of this disclosure and many of the attendant advantages thereof will be readily obtained as the same becomes better understood by reference to the following detailed description when considered in connection with the accompanying drawings, wherein.

DETAILED DESCRIPTION

In one embodiment, there is provided a computed tomography (CT) imaging apparatus, comprising: (1) an X-ray source configured to emit X-rays; (2) a plurality of photon-counting detectors (PCDs) arranged in a circular ring between the X-ray source and a CT detector; and (3) processing circuitry configured to cause the X-ray source and the CT detector to perform a helical scan of an object to obtain projection data; extract, from the obtained projection data, a plurality of sets of projection data corresponding to a plurality of X-ray tube positions of the helical scan; and combine the plurality of sets of extracted projection data to obtain a scanogram.

In another embodiment, there is provided a computed tomography (CT) imaging apparatus, comprising: (1) an X-ray source configured to emit X-rays; (2) a plurality of photon-counting detectors (PCDs) arranged in a circular ring between the radiation source and a CT detector; and (3) processing circuitry configured to cause the X-ray source and the CT detector to perform a helical scan of an object to obtain projection data; perform reconstruction using the obtained projection data using a shadow-correction method to obtain volume data; and project the volume data at a predetermined viewing angle to obtain a scanogram.

Figure 1:
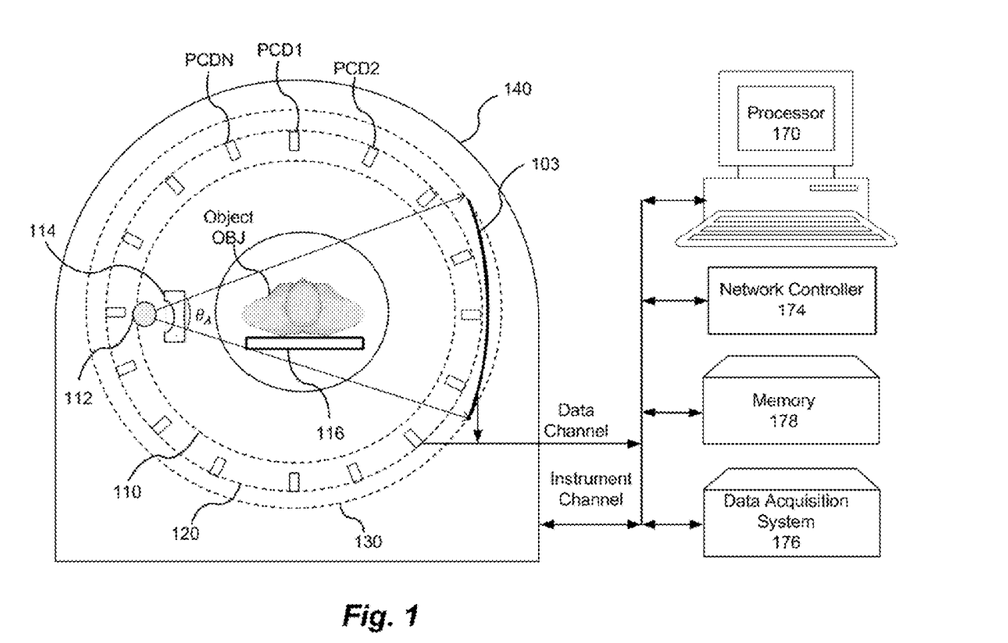
FIG. 1 illustrates a schematic diagram of an implementation of an image reconstruction apparatus having a coupled-ring topology.
Figure 2:
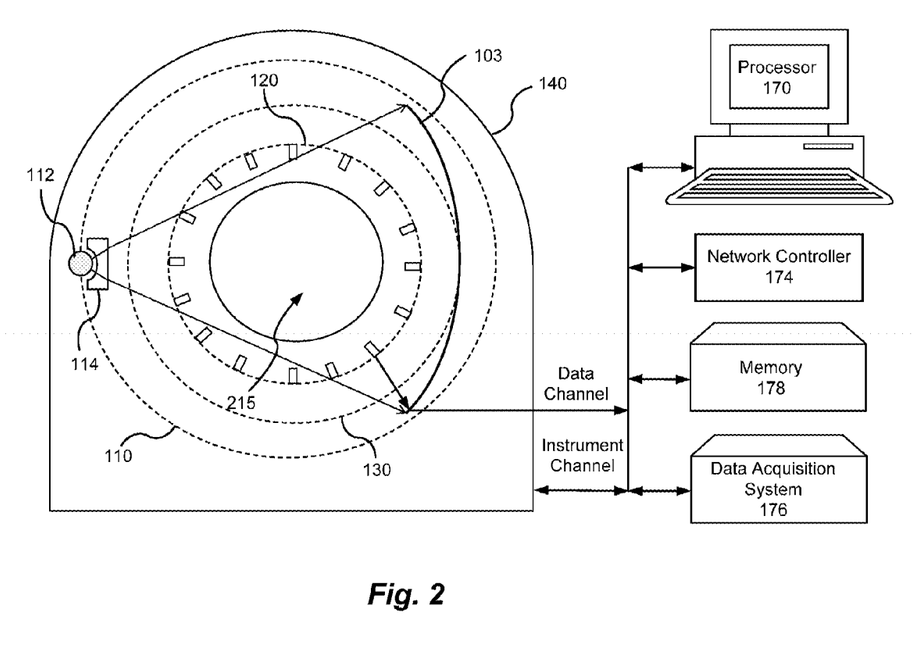
FIG. 2 illustrates a schematic diagram of an implementation of an image reconstruction apparatus having an inner-ring topology.

FIG. 1 and FIG. 2 show schematic views of CT scanner systems with hybrid systems having energy-integrating detectors arranged in a third-generation geometry and photon-counting detectors (PCDs) arranged in a fourth-generation geometry. FIG. 1 shows a coupled-ring topology with the X-ray source 112 inside the ring of PCDs and the X-ray detector unit 103 outside the ring of PCDs, as discussed in U.S. patent application Ser. No. 13/426,903, incorporated herein by reference in its entirety. In contrast, FIG. 2 shows an inner-ring topology with both the X-ray source 112 and the X-ray detector unit 103 outside the ring of PCDs, as discussed in U.S. patent application Ser. No. 14/092,998, incorporated herein by reference in its entirety.

Illustrated in FIG. 1 is an implementation for placing the PCDs in a predetermined fourth-generation geometry in combination with a detector unit 103 in a predetermined third-generation geometry in a CT scanner system. The diagram illustrates relative positions among an object OBJ to be scanned resting on a table 116, an X-ray source 112, a collimator/filter 114, an X-ray detector unit 103, and photon-counting detectors PCD1 through PCDN. The PCDs have a front surface, oriented towards the object OBJ and a back surface oriented away from the object OBJ. X-rays traveling through the object OBJ are either detected by the PCDs (at the front surface) or pass through the spaces between the sparsely arranged PCDs and are detected by the tightly packed energy-integrating detectors in the X-ray detector unit 103.

Also shown in FIG. 1 is circuitry and hardware for acquiring, storing, processing, and distributing X-ray projection data. The circuitry and hardware include: a processor 170, a network controller 174, a memory 178, and a data acquisition system 176.

In one implementation, the X-ray source 112 and the collimator/filter 114 are fixedly connected to a rotational component 110 that is rotatably connected to a gantry 140. The X-ray detector is similarly fixedly connected to a rotational component 130 that is rotatably connected to the gantry 140. While, the PCDs are fixedly connected to a circular component 120 that is fixedly connected to the gantry 140. The gantry 140 houses many pieces of the CT scanner.

The gantry of the CT scanner also includes an open aperture 215 (shown in FIG. 2) enabling the object OBJ that is arranged on a table 116 positioned in a projection plane of the X-rays traveling from the X-ray source to the PCDs and detector unit 203. The "projection plane" is a volume wherein X-rays pass from the X-ray source 112 to the detectors including the PCDs and the detector unit 103. The "object space" is the intersection of the projection plane and the open aperture 215 of the gantry. The "image space" includes the union of projection planes corresponding to all projection angles of the X-ray source 112 as the X-ray source 112 rotates around the aperture of the gantry. The image space is generally larger than the object space enabling image reconstruction for a volume extending beyond the dimension of the object.

A scan is performed when an object OBJ occupies the object space and the X-ray source is rotated through a series of projection angles with the CT scanner acquiring projection data of the X-ray transmission/attenuation through the object OBJ at each projection angle.

In general, the photon-counting detectors PCD1 through PCDN each output a photon count for each of a predetermined number of energy bins. In addition to the photon-counting detectors PCD1 through PCDN arranged in the fourth-generation geometry, the implementation shown in FIG. 1 includes a detector unit 103 having energy-integrating detectors arranged in a conventional third-generation geometry. The detector elements in the detector unit 103 can be more densely placed along the detector unit surface than the photon-counting detectors.

In one implementation, the photon-counting detectors are sparsely placed around the object OBJ in a predetermined geometry such as a circle. For example, the photon-counting detectors PCD1 through PCDN are fixedly placed on a predetermined second circular component 120 in a gantry. In one implementation, the photon-counting detectors PCD1 through PCDN are fixedly placed on the circular component 120 at predetermined equidistant positions. In an alternative implementation, the photon-counting detectors PCD1 through PCDN are fixedly placed on the circular component 120 at predetermined non-equidistant positions. The circular component 120 remains stationary with respect to the object OBJ and does not rotate during the data acquisition.

Both the X-ray source 112, collimator 114 (e.g., a bow-tie filter), and the detector unit 103 rotate around the object OBJ while the photon-counting detectors PCD1 through PCDN are stationary with respect to the object OBJ. In one implementation, the X-ray source 112 projects X-ray radiation with a predetermined source fan beam angle $\theta_A$ towards the object OBJ while the X-ray source 112 rotates around the object OBJ outside the sparsely placed photon-counting detectors PCD1 through PCDN. Furthermore, the detector unit 103 is mounted at a diametrically opposed position from the X-ray source 112 across the object OBJ and rotates outside the stationary circular component 120, on which the photon-counting detectors PCD1 through PCDN are fixed in a predetermined sparse arrangement.

In one implementation, the X-ray source 112 optionally travels a helical path relative to the object OBJ, wherein the table 116 moves the object OBJ linearly in a predetermined direction perpendicular to the rotational plane of the rotational portion 110 as the rotational portion 110 rotates the X-ray source 112 and detector unit 103 in the rotational plane.

The motion of the rotational portion 110 around the object OBJ is controlled by a motion control system. The motion control system can be integrated with a data acquisition system or can be separate providing one way information regarding the angular position of the rotational portion 110 and the linear position of the table 116. The motion control system can include position encoders and feedback to control the position of the rotational portion 110 and the table 116. The motion control system can be an open loop system, a closed loop system, or a combination of an open loop system and a closed loop system. The motion control system can use linear and rotary encoders to provide feedback related to the position of the rotational portion 110 and the position of the table 116. The motion control system can use actuators to drive the motion of the rotational portion 110 and the motion of the table 116. These positioners and actuators can include: stepper motors, DC motors, worm drives, belt drives, and other actuators known in the art.

The CT scanner also includes a data channel that routes projection measurement results from the photon counting detectors and the detector unit 103 to a data acquisition system 176, a processor 170, memory 178, network controller 174. The data acquisition system 176 controls the acquisition, digitization, and routing of projection data from the detectors. The data acquisition system 176 also includes radiography control circuitry to control the rotation of the annular rotational portion 110 and 130. In one implementation data acquisition system 176 will also control the movement of the table 116, the operation of the X-ray source 112, and the operation of the X-ray detectors. The data acquisition system 176 can be a centralized system or alternatively it can be a distributed system. In an implementation, the data acquisition system 176 is integrated with the processor 170. The processor 170 performs functions including reconstructing images from the projection data, pre-reconstruction processing of the projection data, and post-reconstruction processing of the image data.

The pre-reconstruction processing of the projection data can include correcting for detector calibrations, detector nonlinearities, polar effects, noise balancing, and material decomposition.

Post-reconstruction processing can include filtering and smoothing the image, volume rendering processing, and image difference processing as needed. The image reconstruction process can be performed using filtered back-projection, iterative image reconstruction methods, or stochastic image reconstruction methods. Both the processor 170 and the data acquisition system 176 can make use of the memory 178 to store, e.g., projection data, reconstructed images, calibration data and parameters, and computer programs.

The processor 170 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory may be non-volatile, such as ROM, EPROM, EEPROM or FLASH memory. The memory can also be volatile, such as static or dynamic RAM, and a processor, such as a microcontroller or microprocessor, may be provided to manage the electronic memory as well as the interaction between the FPGA or CPLD and the memory.

Alternatively, the CPU in the reconstruction processor may execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

In one implementation, the reconstructed images can be displayed on a display. The display can be an LCD display, CRT display, plasma display, OLED, LED or any other display known in the art.

The memory 178 can be a hard disk drive, CD-ROM drive, DVD drive, FLASH drive, RAM, ROM or any other electronic storage known in the art.

The network controller 174, such as an Intel Ethernet PRO network interface card from Intel Corporation of America, can interface between the various parts of the CT scanner. Additionally, the network controller 174 can also interface with an external network. As can be appreciated, the external network can be a public network, such as the Internet, or a private network such as an LAN or WAN network, or any combination thereof and can also include PSTN or ISDN sub-networks. The external network can also be wired, such as an Ethernet network, or can be wireless such as a cellular network including EDGE, 3G and 4G wireless cellular systems. The wireless network can also be WiFi, Bluetooth, or any other wireless form of communication that is known.

In one implementation, the X-ray source 112 is a single source emitting a broad spectrum of X-ray energies. In another implementation, the X-ray source 112 is configured to perform a kV-switching function for emitting X-ray radiation at a predetermined high-level energy and at a predetermined low-level energy. In still another embodiment, the X-ray source 112 includes multiple X-ray emitters, each emitter being spatially and spectrally distinct.

The detector unit 103 can use energy-integrating detectors such as scintillation elements with photo-multiplier tubes or avalanche photo-diodes to detect the resultant scintillation photons from scintillation events resulting from the X-ray radiation interacting with the scintillator elements. The scintillator elements can be crystalline (e.g., NaI(Tl), CsI (Tl), CsI(Na), CsI(pure), CsF, KI(Tl), LiI(Eu), $BaF_2$, $CaF_2$ (Eu), ZnS(Ag), $CaWO_4$, $CdWO_4$, YAG(Ce), $Y_3Al_5O_{12}$(Ce), GSO, LSO, $LaCl_3$(Ce), $LaBr_3$(Ce), LYSO, BGO, $LaCl_3$ (Ce), $LaBr_3$(Ce), $C_{14}H_{10}$, $C_{14}H_{12}$, and $C_{10}H_8$), an organic liquid (e.g., an organic solvent with a fluor such as p-terphenyl ($C_{18}H_{14}$), PBD ($C_{20}H_{14}N_2O$), butyl PBD ($C_{24}H_{22}N_2O$), or PPO ($C_{15}H_{11}NO$)), a plastic (e.g., a flour suspended in a solid polymer matrix), or other know scintillator.

The PCDs can use a direct X-ray radiation detectors based on semiconductors, such as cadmium telluride (CdTe), cadmium zinc telluride (CZT), silicon (Si), mercuric iodide ($HgI_2$), and gallium arsenide (GaAs). Semiconductor based direct X-ray detectors generally have much faster time response than indirect detectors, such as scintillator detectors. The fast time response of direct detectors enables them to resolve individual X-ray detection events. However, at the high X-ray fluxes typical in clinical X-ray applications some pile-up of detection events will occur. The energy of a detected X-ray is proportional to the signal generated by the direct detector, and the detection events can be organized into energy bins yielding spectrally resolved X-ray data for spectral CT.

FIG. 2 illustrates an inner ring topology for a CT scanner. The primary difference between the CT scanner in FIG. 1 and the CT scanner in FIG. 2 is that, in FIG. 2, the X-ray source 112 and the rotational component 110 to which the X-ray source 112 is fixed are outside the circular component 120 to which the PCDs are fixed. In one implementation, the back surface of each PCD is provided a protective rear cover to shield the PCDs from irradiation from behind as the X-ray source 112 travels outside the circular component 120 of the sparsely placed photon-counting detectors.

Both the X-ray source 112, collimator 114 (e.g., a bow-tie filter), and the detector unit 103 rotate around the object OBJ in aperture 215 while the photon-counting detectors PCD1 through PCDN are stationary with respect to the object OBJ in aperture 215. In one implementation, the X-ray source 112 and collimator 114 are mounted on the first rotational component 110 mounted in the gantry 140 so that the X-ray source 112 projects X-ray radiation with a predetermined source fan beam angle $\theta_A$ towards the object OBJ while the X-ray source 112 rotates around the object OBJ outside the sparsely placed photon-counting detectors PCD1 through PCDN. Furthermore, the detector unit 103 having energy-integrating detectors arranged in a third-generation geometry is mounted on the second rotational component 130 that is rotatably fixed to the gantry 140. The detector unit 103 is maintained at a position diametrically opposed position from the X-ray source 112 with the object OBJ in the intermediary space between the X-ray source 112 and the detector unit 103—the rotational components 110 and 130 rotating outside the stationary circular component 120, on which the photon-counting detectors PCD1 through PCDN are fixed in a predetermined sparse arrangement.

Before a clinical CT scan, a scanogram is performed to locate anatomical landmarks and anatomical regions for a scan prescription. During the scanogram, the X-ray tube and the detector remain stationary when the patient bed travels at a constant speed. The obtained scanogram image is similar to a radiograph.

High-quality scanograms provide sufficient information to localize body structures and enable an efficient scan prescription for subsequent CT scans. Therefore, high quality scanograms can reduce dose and overhead, improve image quality, and are essential for all CT scanners, including a hybrid scanner that includes a ring of sparse, fixed photon-counting detectors (PCDs), and an X-ray source and CT detector that rotate together.

As shown in FIG. 1, in the coupled-ring photon-counting CT scanner, photon-counting detectors (PCDs) are sparsely distributed in front of the third-generation detector and behind the X-ray source. FIG. 2 illustrates, in the inner-ring photon-counting CT scanner, that PCDs are sparsely distributed in front of both the third-generation detector and the X-ray source. Thus, during scanogram scans, these PCDs create shadows on the third-generation detector.

Figure 3:
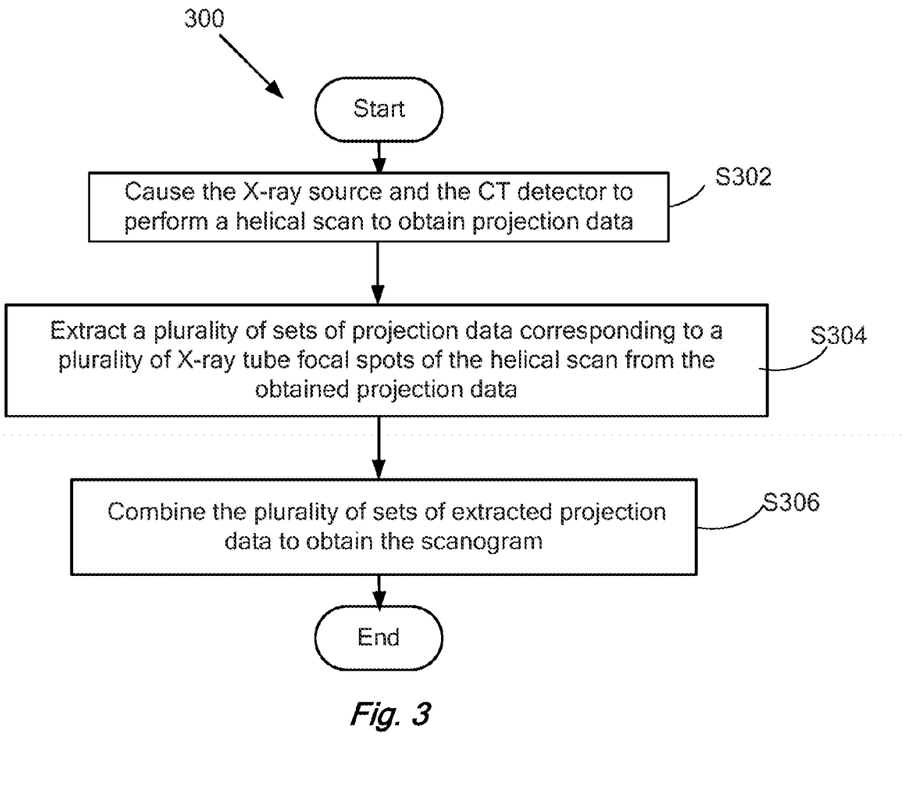
FIG. 3 illustrates an exemplary embodiment of a shadow reduction process using a helical scan method by way of a flowchart.
Figure 8A:
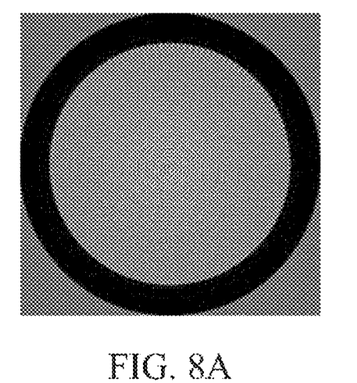
FIGS. 8A and 8B illustrate artifacts to due shadow effects from PCDs.
Figure 8B:
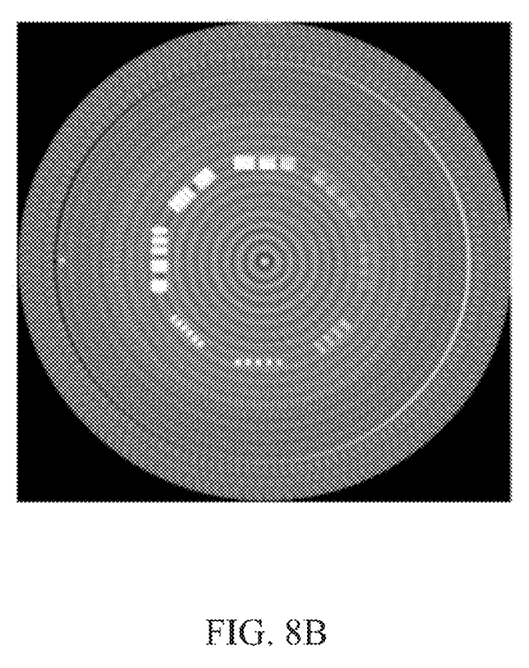

Referring to FIG. 3, a flowchart 300 is shown describing one embodiment performed by processing circuitry for reducing the shadows effects from the sparsely distributed PCDs. In this regard, note that the shadow effects can be manifest as artifacts in the image domain after reconstruction, and as missing data in the sinogram domain before reconstruction. Since, in one embodiment, a scanogram is generated from projection data directly, the shadow effects in the scanogram are indicated or measured by missing projection data. For embodiments involving reconstructing a helical scan (with shadow correction) and forward projection to generate the scanogram (see, e.g., FIG. 6), the image-domain artifacts due to shadow effects can be significant if not corrected. See FIG. 8A, which illustrates ringing/ripple-like artifacts in a scan of a uniform water phantom due to shadow effects, and FIG. 8B, which illustrates similar artifacts due to shadow effects of PCDs.

In step S302, the processing circuitry causes the radiation source and the CT detector to perform a helical scan to obtain projection data. The processing circuitry performs a low-dose (e.g., using low mA) helical scan of the object, as the X-ray source and the CT detector are rotating. The dose of the low-dose scan is less than that of a regular helical CT scan performed to image a target portion of a patient. The dose of the regular helical scan depends on the scan targets, the scan protocols, and the reconstruction methods. Moreover, the dose of the regular helical scan varies between different vendors and models. Usually, CT vendors provide guidelines on the recommended protocol and the dose information to users and regulatory agencies. For example, a typical effective dose (in mSv) to the whole body for a regular CT scan can vary from 1-2 for a head CT scan to 20 for a neonatal abdominal CT scan.

Figure 4:
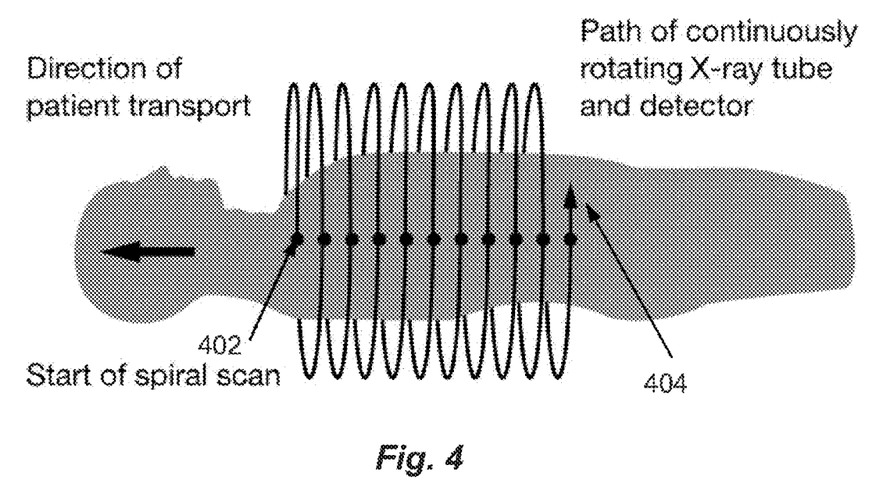
FIG. 4 illustrates an exemplary graph of the helical scan.

In third-generation X-ray scanners, the detectors are mounted on the gantry, opposite the X-ray source, while in the fourth-generation scanners, the detectors are arranged in a fixed ring around the body. As FIG. 4 shows, by continuously rotating the X-ray tube from a start point 402 to an end point 404, the X-ray source traverses a spiral or helical trajectory with respect to the body. As a result of the rotation, a plurality of views are acquired by the helical scan, each view including projection data collected at a different angular and/or axial position of the X-ray radiation source.

In step S304, the processing circuitry extracts, from the obtained projection data, a plurality of sets of projection data corresponding to a plurality of X-ray tube positions of the helical scan. For example, projection data is extracted corresponding to the X-ray tube being above the patient at a predetermined view angle.

Figure 5A:
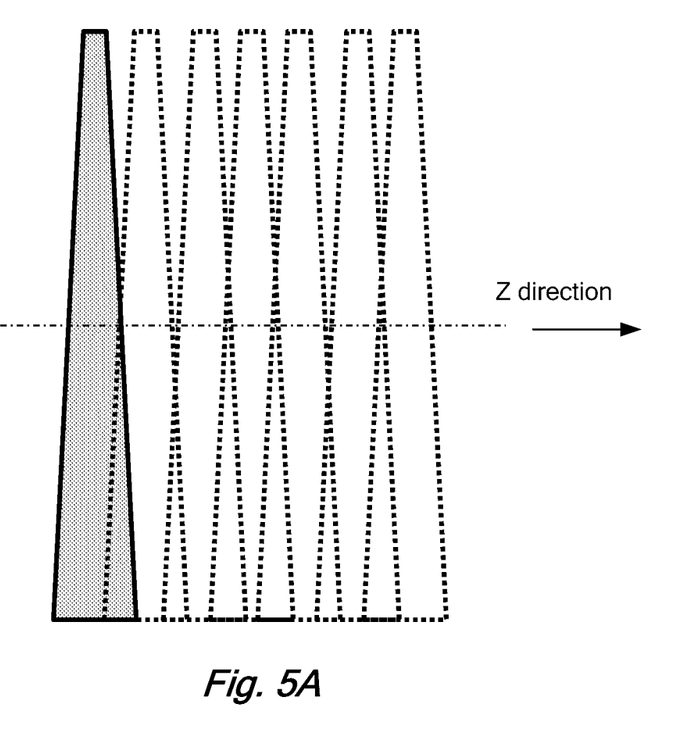
FIG. 5A illustrates an exemplary view of trapezoidal patterns of the helical scan.

In step S306, the processing circuitry combines the plurality of sets of extracted projection data to obtain a scanogram. The sets of extracted projection data are patched together along the long axis (Z-direction in FIG. 5) of the patient to form a scanogram.

Figure 5B:
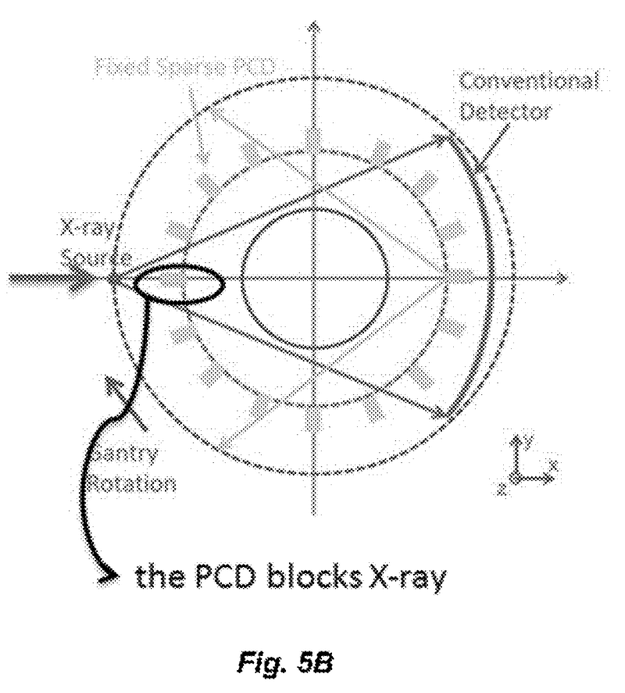
FIG. 5B illustrates an exemplary view of the PCD blocking the X-ray.
Figure 5C:
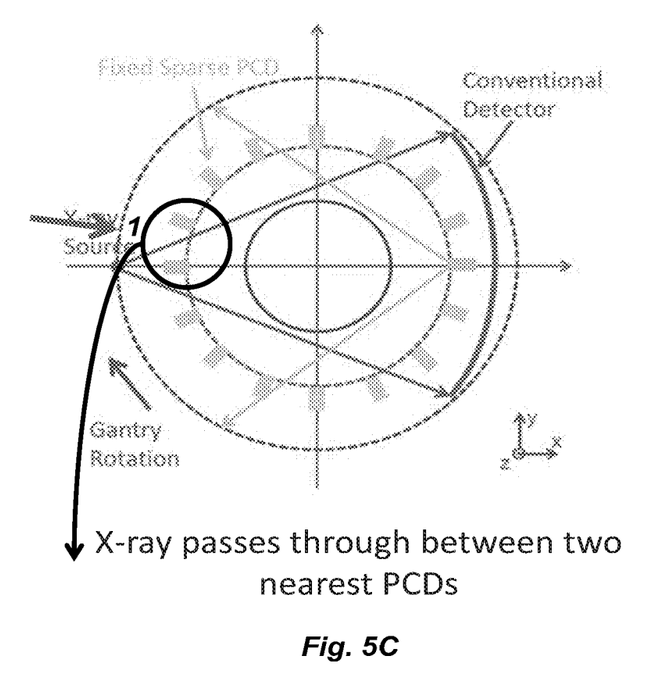
FIG. 5C illustrates an exemplary view of the PCD not blocking the X-ray.

FIG. 5A illustrates an exemplary graph of acquired projection data from the helical scan. In each rotation of the helical scan, the projection data that corresponds to the X-ray tube being at a predetermined view is extracted. If a PCD is blocking the X-ray tube at a given scanogram angle, as shown in FIG. 5B, another viewing angle is used to bypass the shadows of the PCDs. FIG. 5C illustrates an exemplary graph of a view angle that is not blocked by the PCDs. In FIG. 5C, the X-ray source moves to a position 1 and the X-rays passes through a gap between two nearest PCDs without being blocked by any PCDs. The extracted projection data from the helical scan, which is not blocked by the PCDs, is combined to generate a complete scanogram.

Figure 6:
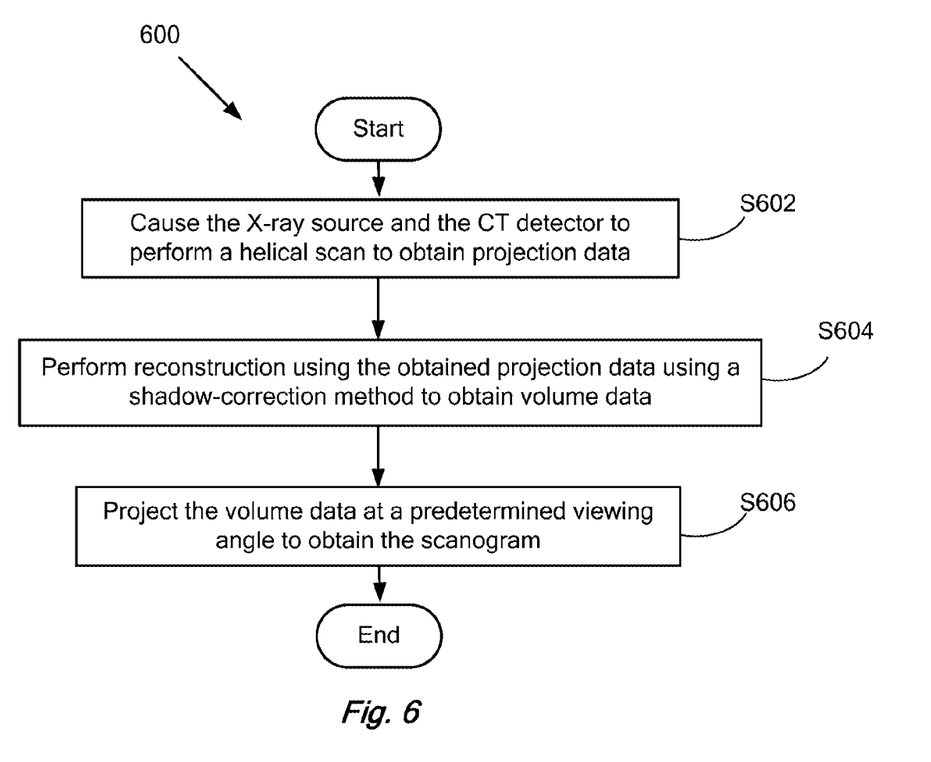
FIG. 6 illustrates another exemplary embodiment of a shadow reduction process using a helical scan method by way of a flowchart.

Referring now to FIG. 6, a flowchart 600 is shown describing another embodiment performed by processing circuitry for obtaining a scanogram and reducing the effects of shadows from the sparsely distributed PCDs on the collected scanogram data.

Step S602 is similar to step S302 in the previous embodiment.

In step S604, the processing circuitry performs reconstruction using the obtained projection data using a shadow-correction method to obtain volume data. One shadow-correction method is to interpolate the shadowed data and reconstruct the interpolated data. Another shadow-correction method is to reconstruct the projection data with matching calibration data. The shadow-correction method was described in U.S. patent application Publication Ser. No. 14/092,998, the contents of which are incorporated herein by reference.

Figure 7:
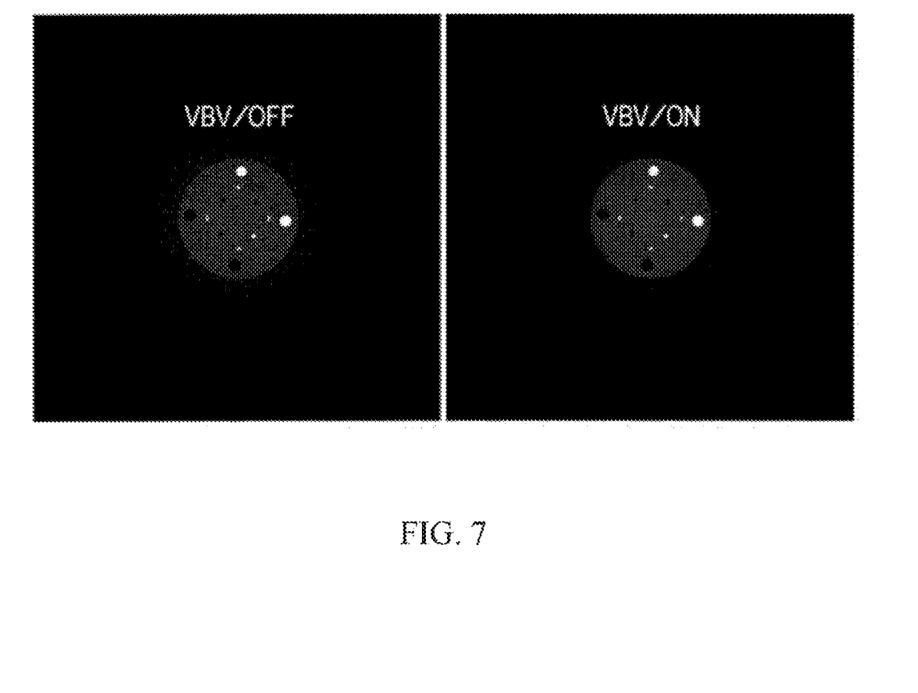
FIG. 7 illustrates a shadow-correction method.

Now referring to FIG. 7, an effect of a view-by-view correction is shown in an exemplary image reconstructed from the data acquired by embodiments for placing the photon-counting detectors (PCDs) in a predetermined fourth-generation geometry in combination with detectors in a predetermined third-generation geometry in the CT scanner system according to one embodiment. A view-by-view correction is necessary for the third-generation detector in the embodiments described above. In general, the view-by-view correction for the measured data from an energy-integrating detector is necessitated by the fourth-generation geometry of the photon-counting detectors. Since X-ray source 112 travels over a predetermined path that is radially outside of the sparsely located photon counting detectors, the fixedly positioned photon counting detectors PCD1 through PCDN block some of the emitted X-ray depending upon the angle of the X-ray source with respect to the photon counting-detectors PCDI through PCDN.

Because of the blockage, the air calibration is necessary depending upon the view angle. In some detail, air scan data is collected for every element of the energy integrating detector in the above described embodiments using the same scan parameters as the future actual scan for image reconstruction. The air scan may be performed either at a predetermined calibration interval or at the beginning or end of the actual scan without an object or a patient. After the actual scan, the above-described air scan data is deducted from the actually scanned energy-integration data, usually in a log scale. For an improved view-by-view correction, the air calibration scan data may be determined based upon an average from multiple air scans. The calibration is not necessarily limited to the air calibration and includes other calibrations such as water or any known phantom calibrations.

FIG. 7 compares the effect in two images with (VBV/ON) or without (VBV/OFF) the view-by-view correction. The image on the right, labeled VBV/ON, has been reconstructed with the view-by-view correction. The image on the left, labeled VBV/OFF, has been reconstructed without the view-by-view correction.

By the same token, the spectral data is optionally corrected for each view based upon blockage of the radiation caused by the energy differentiating detectors. Since the X-ray source travels outside the sparsely placed photon counting detectors and the X-ray travels between the two adjacent ones of the photon counting detectors before reaching the detecting surface of a particular photon counting detector, certain blockage by other photon-counting detectors is optionally taken into account to correct the acquired spectral data.

In step S606, the processing circuitry projects the volume data at a predetermined viewing angle to obtain the scanogram. For any given viewing angle, the reconstructed image provides the line integral of the attenuation along that path. Then Beer's Law, with the incident spectrum information, which is provided by the manufacturer, and attenuation coefficients, which can be theoretically or experimentally obtained, can be used to calculate/project the scanogram.

In particular, a scanogram is generated by forward-projecting the volume data, e.g., calculating line integrals of the volume data alone a line (Radon transform) representing the X-ray tube and detector positions. For example, if the volume data is represented as $\mu(x,y,z)$ for coordinates $(x,y,z)$, the scanogram can be generated with the tube at a fixed position. For every detector channel, the integration line L is between the X-ray tube and the detector channel. Thus, the scanogram signal for that particular channel is given by the integration of $\mu(x,y,z)$ over L, or $\int_L dL \times \mu(x, y, z)$.

The processing circuitry can prescribe mA/kVp modulations in spectral diagnostic scans based on the reconstructed data. The prescription of the mA/kVp modulations based on the reconstructed helical scan data provides more accurate contour information about the object to be scanned than a prescription based on the scanograms from only a few views.

While certain implementations have been described, these implementations have been presented by way of example only, and are not intended to limit the scope of this disclosure. The novel devices, systems and methods described herein may be embodied in a variety of other forms; furthermore, various omissions, substitutions, and changes in the form of the devices, systems and methods described herein may be made without departing from the spirit of this disclosure. The accompanying claims and their equivalents are intended to cover.

The invention claimed is:

1. A computed tomography (CT) imaging apparatus, comprising:
   an X-ray source configured to emit X-rays;
   a plurality of photon-counting detectors (PCDs) arranged in a circular ring between the X-ray source and a CT detector; and
   processing circuitry configured to
   cause the X-ray source and the CT detector to perform a helical scan of an object to obtain projection data;
   extract, from the obtained projection data, a plurality of sets of projection data corresponding to a plurality of X-ray tube positions of the helical scan; and
   combine the plurality of sets of extracted projection data to obtain a scanogram.

2. The apparatus according to claim 1, wherein the processing circuitry is further configured to cause the helical scan to be performed using a dose lower than a dose used for a helical scan performed to obtain a CT image of the object.

3. The apparatus according to claim 1, wherein the processing circuitry is further configured to extract the plurality of sets of projection data at the plurality of X-ray tube positions to minimize effects of shadows caused by the PCDs.

4. The apparatus of claim 1, wherein the X-ray source includes two X-ray emitters that are spatially and spectrally distinct.

5. The apparatus of claim 1, wherein the X-ray source is configured to perform kV-switching and modulation.

6. A method to obtain a scanogram for a hybrid scanner that includes a ring of sparse, fixed photon-counting detectors (PCDs) and an X-ray source and a CT detector that rotate together, the method comprising:
   causing the X-ray source and the CT detector to perform a helical scan of an object to obtain projection data;
   extracting, from the obtained projection data, a plurality of sets of projection data corresponding to a plurality of X-ray tube positions of the helical scan; and
   combining the plurality of sets of extracted projection data to obtain the scanogram.

7. The method according to claim 6, wherein the step of performing the helical scan further comprises performing a helical scan using a dose lower than a dose used for a helical scan performed to obtain a CT image of the object.

8. The method according to claim 6, wherein the combining step further comprises extracting the plurality of sets of projection data at the plurality of X-ray tube positions to minimize effects of shadows caused by the PCDs.

9. A computed tomography (CT) imaging apparatus, comprising:
   an X-ray source configured to emit X-rays;
   a plurality of photon-counting detectors (PCDs) arranged in a circular ring between the X-ray source and a CT detector; and
   processing circuitry configured to
   cause the X-ray source and the CT detector to perform a helical scan of an object to obtain projection data;
   perform reconstruction using the obtained projection data using a shadow-correction method to obtain volume data; and
   project the volume data at a predetermined viewing angle to obtain a scanogram.

10. The apparatus according to claim 9, wherein the processing circuitry is further configured to cause the helical scan to be performed using a dose lower than a dose used for a helical scan performed to obtain a CT image of the object.

11. The apparatus of claim 10, wherein the X-ray source includes two X-ray emitters that are spatially and spectrally distinct.

12. The apparatus of claim 10, wherein the X-ray source is configured to perform kV-switching and modulation.

13. A method to obtain a scanogram for a hybrid scanner that includes a ring of sparse, fixed photon-counting detectors (PCDs) and an X-ray source and a CT detector that rotate together, the method comprising:
   causing the X-ray source and the CT detector to perform a helical scan of an object to obtain projection data;
   performing reconstruction using the obtained projection data using a shadow-correction method to obtain volume data; and
   projecting the volume data at a predetermined viewing angle to obtain the scanogram.

14. The CT method according to claim 13, wherein the step of performing the helical scan further comprises performing a helical scan using a dose lower than a dose used for a helical scan performed to obtain a CT image of the object.

* * * * *